US 8,586,299 B2

(12) United States Patent
Will et al.

(10) Patent No.: US 8,586,299 B2
(45) Date of Patent: *Nov. 19, 2013

(54) ALLELE-SPECIFIC AMPLIFICATION

(75) Inventors: Stephen G. Will, Rotkreuz (CH); Alison Tsan, Castro Valley, CA (US); Nicolas Newton, Oakland, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 446 days.

This patent is subject to a terminal disclaimer.

(21) Appl. No.: 12/582,068

(22) Filed: Oct. 20, 2009

(65) Prior Publication Data

US 2010/0099110 A1  Apr. 22, 2010

Related U.S. Application Data

(60) Provisional application No. 61/106,783, filed on Oct. 20, 2008.

(51) Int. Cl.
| | | |
|---|---|---|
| C12Q 1/68 | (2006.01) | |
| C12P 19/34 | (2006.01) | |
| C07H 21/02 | (2006.01) | |
| C07H 21/04 | (2006.01) | |

(52) U.S. Cl.
USPC .......... 435/6.1; 435/91.2; 536/23.1; 536/24.3

(58) Field of Classification Search
None
See application file for complete search history.

(56) References Cited

U.S. PATENT DOCUMENTS

| | | | |
|---|---|---|---|
| 5,137,806 A | 8/1992 | Le Maistre et al. | |
| 5,210,015 A | 5/1993 | Gelfand et al. | |
| 5,521,301 A | 5/1996 | Wallace et al. | |
| 5,595,890 A | 1/1997 | Newton et al. | |
| 5,639,611 A | 6/1997 | Wallace et al. | |
| 5,990,303 A | 11/1999 | Seela | |
| 6,001,611 A | 12/1999 | Will | |
| 7,135,291 B2 | 11/2006 | Sagawa et al. | |
| 7,408,051 B2 | 8/2008 | Ma et al. | |

FOREIGN PATENT DOCUMENTS

| | | |
|---|---|---|
| EP | 0974672 B1 | 4/2003 |
| WO | 0043544 A1 | 7/2000 |
| WO | 2007127992 A2 | 11/2007 |
| WO | 2007127992 A3 | 11/2007 |
| WO | EP2009007463 | 2/2010 |

OTHER PUBLICATIONS

Whitcombe, D. et al., Nature Biotech., vol. 17, pp. 804-807 (1999).*
Newton, C.R. et al., Nucl. acids res., vol. 17, pp. 2503-2516 (1989).*
Sapio, M. R. et al., Eur. J. Endocrinol., vol. 154, pp. 341-348 (2006).*
Kwok, S. et al., PCR Meth. appl., vol. 3, pp. S39-S47 (1994).*
Gaster, Jens, et al., 2005, "Tuning Single Nucleotide Discrimination in Polymerase Chain Reactions (PCRs): Synthesis of Primer Probes Bearing Polar 4'—C-Modifications and Their Application in Allele-Specific PCR", Chemistry: a European Journal, 11:1861-1870.

* cited by examiner

*Primary Examiner* — Teresa E Strzelecka
(74) *Attorney, Agent, or Firm* — David J. Chang

(57) ABSTRACT

The present invention includes a method of allele-specific amplification, utilizing an allele-specific oligonucleotide, at least partially complementary to more than one variant of the target sequence, but having a 3'-terminal nucleotide complementary to only one variant of the target sequence and having at least one nucleotide with a base covalently modified at the exocyclic amino group, wherein the allele-specific oligonucleotide is extended by a nucleotide-incorporating biocatalyst predominantly when hybridized to the variant of the target sequence for which it has said complementary 3'-terminal nucleotide.

13 Claims, 7 Drawing Sheets

SEQUENCE LISTING

```
<160> NUMBER OF SEQ ID NOS: 18

<210> SEQ ID NO 1
<211> LENGTH: 109
<212> TYPE: DNA
<213> ORGANISM: Homo sapiens

<400> SEQUENCE: 1
agtaaaaata ggtgattttg gtctagctac agagaaatct cgatggagtg ggtcccatca    60
gtttgaacag ttgtctggat ccattttgtg gatggtaaga ttgaggcta              109

<210> SEQ ID NO 2
<211> LENGTH: 110
<212> TYPE: DNA
<213> ORGANISM: Homo sapiens

<400> SEQUENCE: 2
agtaaaaata ggtgattttg gtctagctac agtgaaatct cgatggagtg ggtcccatca    60
gtttgaacag ttgtctggat ccattttgtg gatggtaaga attgaggcta             110

<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
agtaaaaata ggtgattttg gtctagctac aga                                33

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (31)..(31)
<223> OTHER INFORMATION: N6-benzyl-dA

<400> SEQUENCE: 4
agtaaaaata ggtgattttg gtctagctac aga                                33
```

```
<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (31)..(31)
<223> OTHER INFORMATION: N6-para-tert-butyl-benzyl-dA

<400> SEQUENCE: 5
agtaaaaata ggtgattttg gtctagctac aga                                33

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (25)..(25)
<223> OTHER INFORMATION: N6-benzyl-dA

<400> SEQUENCE: 6
tagcctcaat tcttaccatc cacaa                                         25

<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (33)..(33)
<223> OTHER INFORMATION: N6-para-tert-butyl-benzyl-dA

<400> SEQUENCE: 7
agtaaaaata ggtgattttg gtctagctac aga                                33

<210> SEQ ID NO 8
<211> LENGTH: 33
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (29)..(29)
<223> OTHER INFORMATION: N6-para-tert-butyl-benzyl-dA
<220> FEATURE:
<221> NAME/KEY: modified_base
<222> LOCATION: (33)..(33)
<223> OTHER INFORMATION: N6-para-tert-butyl-benzyl-dA

<400> SEQUENCE: 8
agtaaaaata ggtgattttg gtctagctac aga                                33

<210> SEQ ID NO 9
<211> LENGTH: 10
<212> TYPE: DNA
<213> ORGANISM: Artificial Sequence
<220> FEATURE:
<223> OTHER INFORMATION: Description of Artificial Sequence: Synthetic
      probe
```

-continued

```
<400> SEQUENCE: 9
tcgatggagt                                                           10

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (33)..(33)
<223> OTHER INFORMATION: N6-benzyl-dA

<400> SEQUENCE: 10
agtaaaaata ggtgattttg gtctagctac aga                                 33

<210> SEQ ID NO 11
<211> LENGTH: 31
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (27)..(27)
<223> OTHER INFORMATION: N6-benzyl-dA
<220> FEATURE:
<221> NAME/KEY: modified_base
<222> LOCATION: (31)..(31)
<223> OTHER INFORMATION: N6-benzyl-dA

<400> SEQUENCE: 11
taaaaatagg tgattttggt ctagctacag a                                   31

<210> SEQ ID NO 12
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cccgcgcgga cccactccat cgagagcgcg gg                                  32

<210> SEQ ID NO 13
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cccgcgcgga cccactccat cgagagcgcg gg                                  32

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (25)..(25)
<223> OTHER INFORMATION: N6-benzyl-dA
```

```
<400> SEQUENCE: 14
tagcctcaat tcttaccatc cacaa                                              25

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 15
tctcgatgga gtgggtcc                                                      18

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 16
gggtcccatc agtttgaaca gttgtct                                            27

<210> SEQ ID NO 17
<211> LENGTH: 33
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 17
agtaaaaata ggtgattttg gtctagctac aga                                     33

<210> SEQ ID NO 18
<211> LENGTH: 33
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (31)..(31)
<223> OTHER INFORMATION: N6-para-tert-butyl-benzyl-dA

<400> SEQUENCE: 18
agtaaaaata ggtgattttg gtctagctac aga                                     33
```

ALLELE-SPECIFIC AMPLIFICATION

CROSS-REFERENCE TO RELATED APPLICATION

The present application claims the benefit of provisional application No. 61/106,783 filed Oct. 20, 2008, the content of which is hereby incorporated herein by reference in its entirety.

SEQUENCE LISTING

The instant application contains a Sequence Listing which has been submitted via EFS-Web and is hereby incorporated by reference in its entirety. Said ASCII copy, created on Oct. 16, 2009, is named 25294US.txt, and is 5,171 bytes in size.

FIELD OF THE INVENTION

The invention relates to the field of nucleic acid amplification and specifically, to the field of allele-specific amplification.

BACKGROUND OF THE INVENTION

Allele-specific amplification of nucleic acids allows for simultaneous amplification and analysis of the target sequence. Allele-specific amplification is commonly used when the target nucleic acid is suspected of having one or more subpopulations with a variation (polymorphism) in its sequence. DNA polymorphisms are used in DNA profile analysis (forensics, paternity testing, tissue typing for organ transplants), genetic mapping, as well as detection of rare mutations, such as those occurring in cancer cells in the background of cells with normal DNA.

In a successful allele-specific amplification, the desired variant of the target nucleic acid is amplified, while the other variants are not, at least not to a detectable level. A typical allele-specific amplification assay involves a polymerase chain reaction (PCR) where at least one primer is complementary to the region with a suspected polymorphism. The design of the allele-specific primer is such that primer extension occurs only when a certain variant of the polymorphism is present. In its simplest form, the allele-specific primer has a 3'-terminal nucleotide complementary to the desired variant of the polymorphic nucleotide in the target. Often a single mismatch at the 3'-terminus of the primer is sufficient to preclude amplification of the undesired variants of the target sequence. However, specificity of amplification varies greatly among different 3'-terminal sequences: some mismatches effectively block extension by the polymerase, while others do not, see U.S. Pat. No. 5,639,611.

The success of allelic discrimination depends on the inability of the DNA polymerase to extend mismatched primers. This inability of the DNA polymerase may be modulated by adjusting the reaction conditions to achieve maximum selectivity. Nevertheless, poor selectivity of allele-specific PCR remains a problem for many polymorphic sequences.

One approach to increasing specificity involves engineering amplification primers with an internal mismatched nucleotide or nucleotides. This approach proved successful in some systems, see U.S. Pat. No. 5,137,806.

Another approach to increasing specificity involves chemical modification of the primers. For example, it was found that certain 2'-C and 4'-C modifications of the deoxyribose of some nucleotides in the primer enhance allele discrimination by the polymerase. See Gaster, J. and Marx, A., Chem. Eur. J. 2005, 11:1861-1870. In another study, it was found that allelic discrimination is enhanced by the use of an unnatural pyrimidine base in one of the nucleotides in the primer, specifically, pseudoisocytidine with various substituents in the 6-position of the pyrimidine ring, see U.S. Pat. No. 7,408,051.

In the context of real-time allele-specific PCR, the selectivity of the assay may be measured as the difference in the threshold cycle number (Ct) between the matched and mismatched templates. A greater difference indicates a greater delay in amplification of the mismatched template and thus a greater discrimination between alleles. The modified deoxyribose has been shown to result in Ct differences of between 1 and 14 cycles. The use of pseudoisocytidine resulted in a 7-cycle delay in amplification of the mismatched template. This degree of discrimination is insufficient for many applications, where the sample contains several variants of the template, all competing for amplification. Often the mismatched template is present in much greater amounts than the matched template. For example, in tissue samples, only a small fraction of cells may be malignant and carry the mutation ("matched template"), targeted by the allele-specific amplification assay. The template present in normal cells may be amplified less efficiently, but the overwhelming numbers of normal cells will overcome any delay in amplification and erase any advantage of the mutant template. To detect rare mutations in the presence of the wild-type template, the specificity of the allele-specific amplification assay needs to be improved.

SUMMARY OF THE INVENTION

In a first aspect, the invention relates to an improved method of allele-specific amplification, wherein one or more nucleotides in the allele-specific primer or primers are modified by a covalent linkage of a modifier group to an exocyclic amino group of the nucleobase. The modification may occur internally or at the 3'-end of the primer, or both.

In a second aspect, the invention relates to a method of allele-specific amplification of a variant of a target sequence, which exists in the form of several variant sequences, comprising
(a) providing a sample, possibly containing at least one variant of a target sequence;
(b) providing a first oligonucleotide, at least partially complementary to one or more variants of the target sequence;
(c) providing a second oligonucleotide, at least partially complementary to one or more variants of the target sequence, having at least one 3'-terminal nucleotide complementary to only one variant of the target sequence; wherein said second oligonucleotide incorporates at least one nucleotide with a base covalently modified at the exocyclic amino group;
(d) providing conditions suitable for the hybridization of said first and second oligonucleotides to at least one variant of the target sequence; and
(e) providing conditions suitable for the second oligonucleotide extension by a nucleotide-incorporating biocatalyst; wherein said biocatalyst is capable of extending said second oligonucleotide when it is hybridized to the variant of the target sequence for which it has said complementary 3'-terminal nucleotide, and substantially less when said second oligonucleotide is hybridized to the variant of the target sequence for which it has a non-complementary 3'-terminal nucleotide.

In a third aspect, the invention relates to a method of detecting a variant of a target sequence in a sample, which exists in the form of several variant sequences comprising
(a) hybridizing a first and second oligonucleotides to at least one variant of the target sequence; wherein the first oligonucleotide is at least partially complementary to one or more variant of the target sequence and the second oligonucleotide is at least partially complementary to one or more variant of the target sequence and has a 3'-terminal nucleotide complementary to only one variant of the target sequence, said second oligonucleotide incorporating at least one nucleotide with a base covalently modified at the exocyclic amino group;
(b) extending the second oligonucleotide with a nucleotide-incorporating biocatalyst; wherein said biocatalyst is capable of detectably extending only the oligonucleotide, hybridized to the variant of the target sequence for which it has said complementary 3'-terminal nucleotide; and
(c) detecting the products of said second oligonucleotide extension, wherein the extension signifies the presence of the variant of a target sequence to which the oligonucleotide has a complementary 3'-terminal nucleotide.

In a fourth aspect, the invention relates to a kit for allele-specific amplification of a target sequence, which exists in the form of several variant sequences, comprising
(a) a first oligonucleotide, at least partially complementary to one or more variant of the target sequence; and
(b) a second oligonucleotide, at least partially complementary to one or more variant of the target sequence and having a 3'-terminal nucleotide complementary to only one variant of the target sequence; wherein said second oligonucleotide incorporates at least one nucleotide with a base covalently modified at the exocyclic amino group.

In a fifth aspect, the invention relates to an oligonucleotide for performing an allele-specific amplification of a target sequence, which exists in the form of several variant sequences, comprising
a sequence at least partially complementary to a portion of one or more variants of said target sequence;
a 3'-terminal nucleotide which is complementary to only one variant of said target sequence and
at least one nucleotide with a base covalently modified at the exocyclic amino group.

DETAILED DESCRIPTION OF THE INVENTION

Definitions

Figure 1:
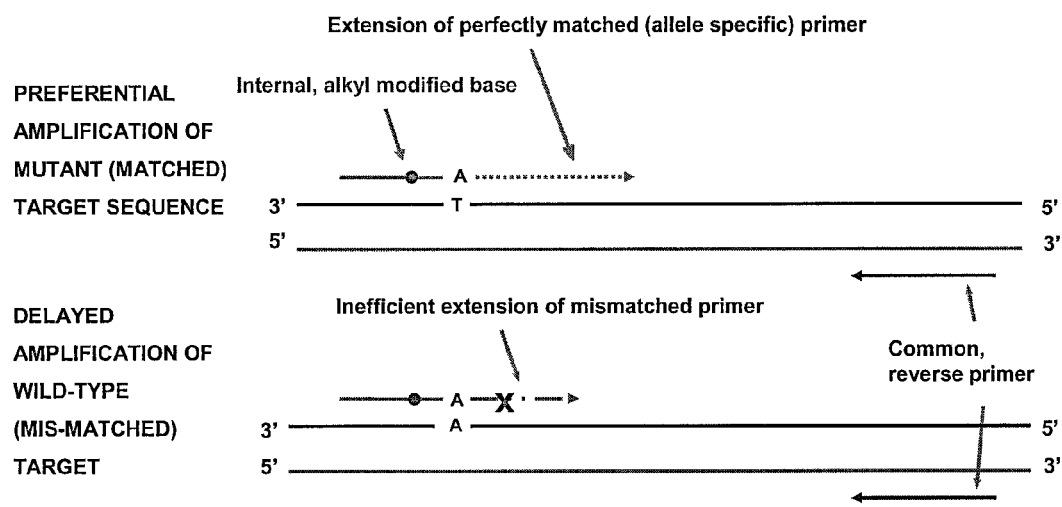
FIG. 1 is a schematic diagram of the allele-specific amplification assay of the present invention.

Unless defined otherwise, all technical and scientific terms used herein have the same meaning as commonly understood by one of ordinary skill in the art to which this invention pertains. In describing and claiming the present invention, the following definitions will be used.

The term "nucleic acid" refers to polymers of nucleotides (e.g., ribonucleotides, deoxyribonucleotides, nucleotide analogs etc.) and comprising deoxyribonucleic acids (DNA), ribonucleic acids (RNA), DNA-RNA hybrids, oligonucleotides, polynucleotides, aptamers, peptide nucleic acids (PNAs), PNA-DNA conjugates, PNA-RNA conjugates, etc., that comprise nucleotides covalently linked together, either in a linear or branched fashion. A nucleic acid is typically single-stranded or double-stranded and will generally contain phosphodiester bonds, although in some cases, nucleic acid analogs are included that may have alternate backbones, including, for example, phosphoramide (Beaucage et al. (1993) Tetrahedron 49(10):1925); phosphorothioate (Mag et al. (1991) Nucleic Acids Res. 19:1437; and U.S. Pat. No. 5,644,048), phosphorodithioate (Briu et al. (1989) J. Am. Chem. Soc. 111:2321), O-methylphosphoroamidite linkages (see Eckstein, Oligonucleotides and Analogues: A Practical Approach, Oxford University Press (1992)), and peptide nucleic acid backbones and linkages (see, Egholm (1992) J. Am. Chem. Soc. 114:1895). Other analog nucleic acids include those with positively charged backbones (Denpcy et al. (1995) Proc. Natl. Acad. Sci. USA 92: 6097); non-ionic backbones (U.S. Pat. Nos. 5,386,023, 5,637,684, 5,602,240, 5,216,141 and 4,469,863) and non-ribose backbones, including those described in U.S. Pat. Nos. 5,235,033 and 5,034, 506. Nucleic acids containing one or more carbocyclic sugars are also included within the definition of nucleic acids (see Jenkins et al. (1995) Chem. Soc. Rev. pp. 169-176), and analogs are also described in, e.g., Rawls, C & E News Jun. 2, 1997 page 35. These modifications of the ribose-phosphate backbone may be done to facilitate the addition of additional moieties such as labels, or to alter the stability and half-life of such molecules in physiological environments.

In addition to the naturally occurring heterocyclic bases that are typically found in nucleic acids (e.g., adenine, guanine, thymine, cytosine, and uracil), nucleotide analogs also may include non-naturally occurring heterocyclic bases, such as those described in, e.g., Seela et al. (1999) Helv. Chim. Acta 82:1640. Certain bases used in nucleotide analogs act as melting temperature (Tm) modifiers. For example, some of these include 7-deazapurines (e.g., 7-deazaguanine, 7-deazaadenine, etc.), pyrazolo[3,4-d]pyrimidines, propynyl-dN (e.g., propynyl-dU, propynyl-dC, etc.), and the like. See, e.g., U.S. Pat. No. 5,990,303, which is incorporated herein by reference. Other representative heterocyclic bases include, e.g., hypoxanthine, inosine, xanthine; 8-aza derivatives of 2-aminopurine, 2,6-diaminopurine, 2-amino-6-chloropurine, hypoxanthine, inosine and xanthine; 7-deaza-8-aza derivatives of adenine, guanine, 2-aminopurine, 2,6-diaminopurine, 2-amino-6-chloropurine, hypoxanthine, inosine and xanthine; 6-azacytidine; 5-fluorocytidine; 5-chlorocytidine; 5-iodocytidine; 5-bromocytidine; 5-methylcytidine; 5-propynylcytidine; 5-bromovinyluracil; 5-fluorouracil; 5-chlorouracil; 5-iodouracil; 5-bromouracil; 5-trifluoromethyluracil; 5-methoxymethyluracil; 5-ethynyluracil; 5-propynyluracil, and the like.

A "nucleoside" refers to a nucleic acid component that comprises a base or basic group (comprising at least one homocyclic ring, at least one heterocyclic ring, at least one aryl group, and/or the like) covalently linked to a sugar moiety (a ribose sugar or a deoxyribose sugar), a derivative of a sugar moiety, or a functional equivalent of a sugar moiety (e.g. a carbocyclic ring). For example, when a nucleoside includes a sugar moiety, the base is typically linked to a 1'-position of that sugar moiety. As described above, a base can be a naturally occurring base or a non-naturally occurring base. Exemplary nucleosides include ribonucleosides, deoxyribonucleosides, dideoxyribonucleosides and carbocyclic nucleosides.

A "nucleotide" refers to an ester of a nucleoside, e.g., a phosphate ester of a nucleoside, having one, two, three or more phosphate groups covalently linked to a 5' position of a sugar moiety of the nucleoside.

A "purine nucleotide" refers to a nucleotide that comprises a purine base, whereas a "pyrimidine nucleotide" refers to a nucleotide that comprises a pyrimidine base.

An "oligonucleotide" refers to a nucleic acid polymer that includes at least two, but typically 5-50 nucleotides and more typically, between 15 and 35 nucleotides. The exact size of an oligonucleotide generally depends on various factors, including the ultimate function or use of the oligonucleotide. Oligonucleotides may be prepared by any suitable method known in the art, including, for example, cloning and restriction digestion of appropriate sequences, or direct chemical synthesis by a method such as the phosphotriester method of Narang et al. (1979) Meth. Enzymol. 68:90-99; the phosphodiester method of Brown et al. (1979) Meth. Enzymol. 68:109-151; the diethylphosphoramidite method of Beaucage et al. (1981) Tetrahedron Lett. 22:1859-1862; the triester method of Matteucci et al. (1981) J. Am. Chem. Soc. 103:3185-3191; automated synthesis methods; the solid support method of U.S. Pat. No. 4,458,066 or any other chemical method known in the art.

A "primer nucleic acid" or "primer" is an oligonucleotide that can hybridize to a template nucleic acid and permit chain extension or elongation using a nucleotide incorporating biocatalyst. Although other primer lengths are sometimes utilized, primers typically range from 15 to 35 nucleotides. Short primer nucleic acids generally utilize cooler temperatures to form sufficiently stable hybrid complexes with template nucleic acids. A primer nucleic acid that is at least partially complementary to a subsequence of a template nucleic acid is typically sufficient to hybridize with the template nucleic acid for extension to occur. However, the success of the extension generally requires greater complementarity (i.e. fewer mismatches with the template) at the 3'-end of the primer. A primer nucleic acid can be labeled, if desired, by incorporating a label detectable by radiological, spectroscopic, photochemical, biochemical, immunochemical, or chemical techniques.

An "extended primer" refers to a primer to which one or more additional nucleotides have been added. "Primer extension" is the action of the enzyme by which additional nucleotides are added to the primer.

A "template nucleic acid", "template" or "target" refers to a nucleic acid to which a primer nucleic acid can hybridize and be extended under suitable conditions. In the context of nucleic acid amplification, "target" is preferably a region of double stranded nucleic acid, consisting of the sequences at least partially complementary to at least two primer sequences and the intervening sequence. A target can also be a single stranded nucleic acid, consisting of a sequence at least partially complementary to one primer and a sequence partially identical to the second primer. Template nucleic acids can exist as isolated nucleic acid fragments or be a part of a larger nucleic acid fragment. Target nucleic acids can be derived or isolated from essentially any source, such as cultured microorganisms, uncultured microorganisms, complex biological mixtures, tissues, sera, ancient or preserved tissues or samples, environmental isolates or the like. Further, template nucleic acids optionally include or are derived from cDNA, RNA, genomic DNA, cloned genomic DNA, genomic DNA libraries, enzymatically fragmented DNA or RNA, chemically fragmented DNA or RNA, physically fragmented DNA or RNA, or the like. Template nucleic acids can also be chemically synthesized using techniques known in the art.

As used herein, a "gene" refers to any segment of DNA associated with a biological function. Thus, genes include coding sequences and optionally, the regulatory sequences required for the expression of the coding sequences.

Nucleic acids are "extended" or "elongated" when additional nucleotides are incorporated into the nucleic acids, for example by a nucleotide incorporating biocatalyst, at the 3' end of a nucleic acid.

A "moiety" or "group" refers to one of the portions into which something, such as a molecule, is divided (e.g., a functional group, substituent group, or the like). For example, a nucleotide typically comprises a base group (e.g., adenine, thymine, cytosine, guanine, uracil, or an analog), a sugar moiety, and one or more phosphate groups.

An "alkyl group" refers to a linear, branched, or cyclic saturated hydrocarbon moiety and includes all positional isomers, e.g., methyl, ethyl, propyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, n-hexyl, cyclohexyl, n-heptyl, n-octyl, 2-ethylhexyl, n-nonyl, n-decyl and the like. An alkyl group typically comprises about 1-20 carbon atoms and more typically comprises about 2-15 carbon atoms. Alkyl groups can be substituted or unsubstituted.

An "alkoxy group" refers to an alkyl group that comprises an oxygen atom and includes, e.g., methoxy, ethoxy, propoxy, butoxy, pentoxy, heptyloxy, octyloxy, and the like.

An "aryl group" refers to a substituent group of atoms or moiety that is derived from an aromatic compound. Exemplary aryl groups include, e.g., phenyl groups, or the like. Aryl groups optionally include multiple aromatic rings (e.g., diphenyl groups, etc.). In addition, an aryl group can be substituted or unsubstituted.

An "aryloxy group" refers an aryl group that comprises an oxygen atom and includes, e.g., phenoxy, chlorophenoxy, methylphenoxy, methoxyphenoxy, butylphenoxy, pentylphenoxy, benzyloxy, and the like.

An "alkyl-aryl group" refers to a group that comprises alkyl and aryl moieties. Examples of the alkyl-aryl groups include benzyl groups, tolyl groups and xylyl groups.

An amplification assay is "selective" or "allele-selective" if it yields a predominance (i.e., a majority but less than 100%) of one product over other possible products. An assay is described as "allele-selective" as long as amplification of the undesired (mismatched) variant of the target sequence is detectable. The term "specific" or "allele-specific" amplification assay is used if one of the possible products is formed exclusively. The assay where amplification of the undesired (mismatched) target is undetectable is called "allele-specific." As the methods of detection become more sensitive, some assays previously known to be allele-specific, turn out to be allele-selective, i.e. some amplification of undesired variants of the target becomes detectable. Therefore, in the context of this invention, the term "allele-specific" is meant to encompass both strictly allele-specific, as well as allele-selective amplification.

A "genotype" refers to all or part of the genetic constitution of a cell or subject, or group of cells or subjects. For example, a genotype includes the particular mutations and/or alleles (e.g., polymorphisms, such as single nucleotide polymorphisms (SNPs) or the like) present at a given locus or distributed in a genome.

A "nucleotide incorporating biocatalyst" or "nucleotide incorporating enzyme" refers to a catalyst (or enzyme) that catalyzes the incorporation of nucleotides into a nucleic acid. Exemplary nucleotide incorporating enzymes include, DNA polymerases, RNA polymerases, terminal transferases, reverse transcriptases, telomerases and the like.

A "thermostable enzyme" refers to an enzyme that is stable (i.e., resists breakdown or denaturation) and retains sufficient catalytic activity when subjected to elevated temperatures for selected periods of time. For example, a thermostable polymerase retains sufficient activity to effect subsequent primer extension reactions, when subjected to elevated temperatures for the time necessary to denature double-stranded nucleic acids. Heating conditions necessary for nucleic acid denaturation are well known in the art and are exemplified in U.S. Pat. Nos. 4,683,202 and 4,683,195. As used herein, a thermostable polymerase is typically suitable for use in a temperature cycling reaction such as the polymerase chain reaction ("PCR"). The examples of thermostable nucleic acid polymerases include *Thermus aquaticus* Taq DNA polymerase, *Thermus* sp. Z05 polymerase, *Thermus flavus* polymerase, *Thermotoga maritima* polymerases, such as TMA-25 and TMA-30 polymerases, Tth DNA polymerase, and the like.

A "modified" enzyme refers to an enzyme comprising an amino acid polymer in which at least one monomer differs from the reference sequence, such as a native or wild-type form of the enzyme or another modified form of the enzyme. Exemplary modifications include monomer insertions, deletions, and substitutions. Modified enzymes also include chimeric enzymes that have identifiable component sequences (e.g., structural or functional domains, etc.) derived from two or more parents. Also included within the definition of modified enzymes are those comprising chemical modifications of the reference sequence. The examples of modified polymerases include G46E E678G CS5 DNA polymerase, G46E L329A E678G CS5 DNA polymerase, G46E L329A D640G S671F CS5 DNA polymerase, G46E L329A D640G S671F E678G CS5 DNA polymerase, a G46E E678G CS6 DNA polymerase, ΔZ05 polymerase, ΔZ05-Gold polymerase, ΔZ05R polymerase, E615G Taq DNA polymerase, E678G TMA-25 polymerase, E678G TMA-30 polymerase, and the like.

The term "5' to 3' nuclease activity" or "5'-3' nuclease activity" refers to an activity of a nucleic acid polymerase, typically associated with the nucleic acid strand synthesis, whereby nucleotides are removed from the 5' end of nucleic acid strand, e.g., *E. coli* DNA polymerase I has this activity, whereas the Klenow fragment does not.

A polymerase that "substantially lacks 5'-3' nuclease activity" refers to a polymerase that has 50% or less (e.g., <25%, <20%, <15%, <10%) 5'-3' nuclease activity than Taq DNA polymerase. Methods of measuring 5'-3' nuclease activity and conditions for measurement are well known in the art. See, e.g., U.S. Pat. No. 5,466,591. Examples of DNA polymerases substantially lacking 5' to 3' nuclease activity include the Klenow fragment of *E. coli* DNA polymerase I; a *Thermus aquaticus* DNA polymerase (Taq) lacking the N-terminal 235 amino acids (e.g., as described in U.S. Pat. No. 5,616,494 and commonly referred to in the art as the "Stoffel fragment"). Other examples include a thermostable DNA polymerase having sufficient deletions (e.g., N-terminal deletions), mutations, or modifications so as to eliminate or inactivate the domain responsible for the 5'-3' nuclease activity. See, e.g., U.S. Pat. No. 5,795,762.

A "label" refers to a moiety attached (covalently or non-covalently), to a molecule and capable of providing information about the molecule. Exemplary labels include fluorescent labels, colorimetric labels, chemiluminescent labels, bioluminescent labels, radioactive labels, mass-modifying groups, antibodies, antigens, biotin, haptens, and enzymes (including peroxidase, phosphatase, etc.).

A "hot start", in the context of a nucleic acid amplification reaction, refers to a protocol, where at least one critical reagent is withheld from the reaction mixture (or, if present in the reaction mixture, the reagent remains inactive) until the temperature is raised sufficiently to provide the necessary hybridization specificity of the primer or primers. A "hot start enzyme" is an enzyme, typically a nucleic acid polymerase, capable of acting as the "withheld" or inactive reagent in a hot start protocol.

A "Watson-Crick base pairing" or simply "base pairing" refers to "conventional" hydrogen bonding within a double-stranded nucleic acid molecule. Watson-Crick base pairing is hyrdrogen bonding between adenine and thymine, between guanine and cytosine, between adenine and uracil, and between analogs of these bases.

Figure 7:
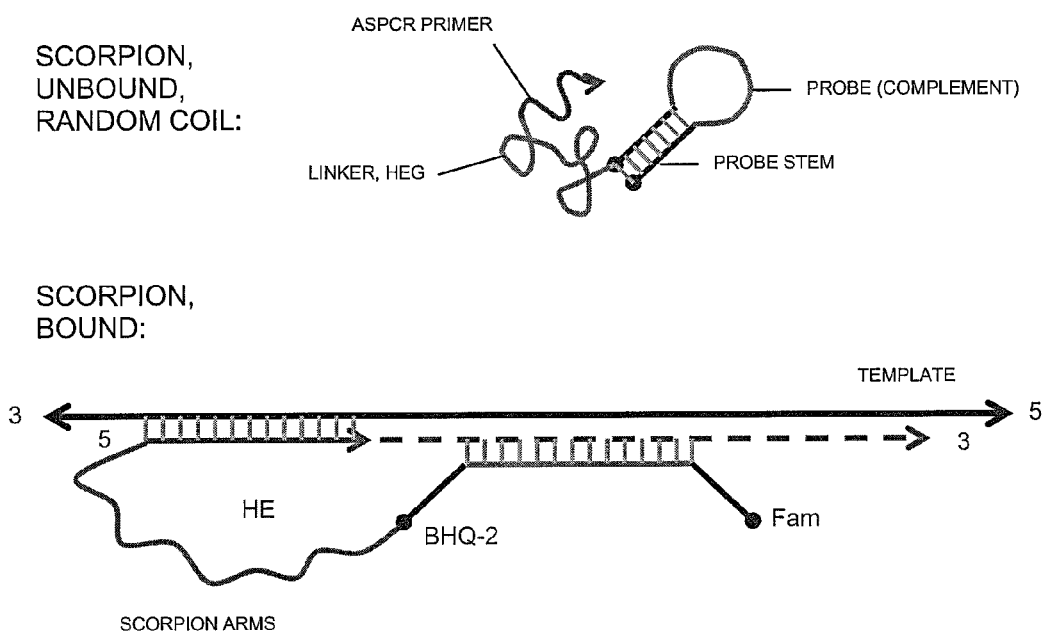
FIG. 7 shows a schematic representation of the structure of a scorpion ARMS format that can be used according to the invention.

The terms "scorpion" or "scorpion-like" denote unimolecular primer-probe combination as described in Whitcombe et al., (1999). Detection of PCR products using self-probing amplicons and fluorescence, Nature Biotech. 17:804-807. Scorpion or scorpion-like primers within the meaning of the present invention incorporate the typical elements of the scorpion, namely a probe portion, a stem loop portion and a primer portion. An example of "scorpion" or "scorpion-like" unimolecular primer-probe format is schematically illustrated in FIG. 7.

As mentioned above, in one aspect, the present invention relates to a method of allele-specific amplification, comprising (a) providing a sample, possibly containing at least one variant of a target sequence; (b) providing a first oligonucleotide, at least partially complementary to more than one variant of the target sequence; (c) providing a second oligonucleotide, at least partially complementary to one or more variants of the target sequence, having a 3'-terminal nucleotide complementary to only one variant of the target sequence; wherein said second oligonucleotide incorporates at least one nucleotide with a base covalently modified at the exocyclic amino group; (d) providing conditions suitable for the hybridization of said first and second oligonucleotides to at least one variant of the target sequence; (e) providing conditions suitable for the oligonucleotide extension by a nucleotide incorporating biocatalyst; wherein said biocatalyst is capable of extending said second oligonucleotide when it is hybridized to the variant of the target sequence for which it has said complementary 3'-terminal nucleotide, and substantially less when said second oligonucleotide is hybridized to the variant of the target sequence for which it has a non-complementary 3'-terminal nucleotide.

The second oligonucleotide, at least partially complementary to one or more variants of the target sequence, having a 3'-terminal nucleotide complementary to only one variant of the target sequence is referred to as a "selective oligonucleotide," "selective primer," or "allele-selective primer." The selective oligonucleotide of the present invention comprises 10-50, more preferably 15-35 nucleotides, the majority of them complementary to a sequence in more then one variant of the target sequence. The 3'-terminal nucleotide of the oligonucleotide is complementary to a variant of the target sequence, that is to be amplified and not complementary to other variants. The selective oligonucleotide of the present invention includes one or more nucleotides with a base, covalently modified at the exocyclic amino group. In some embodiments, the modified-base nucleotide occurs between 1 and 5, but preferably 3 nucleotides upstream of the 3'-terminal nucleotide (also designated as −1, −2, −3, −4, −5 or N−1, N−2, N−3, N−4, N−5 positions herein). In other embodiments, the modified-base nucleotide is the 3'-terminal nucleotide. In some embodiments, the modified-base nucleotide occurs both at the 3'-terminus and at least once more, elsewhere within the oligonucleotide.

The allele-specific primer of the present invention may incorporate various aspects of primer design known in the art. For example, the primer may take the form of a unimolecular primer-probe combination termed "scorpion" and described in Whitcombe et al., (1999) Detection of PCR products using self-probing amplicons and fluorescence, Nature Biotech. 17:804-807. The scorpion primer designed according to the present invention incorporates the typical elements of the scorpion, namely a probe portion, a stem loop portion and a primer portion. Further, in a scorpion designed according to the present invention, the primer portion has a 3' end complementary to the variant position. The primer portion in a scorpion designed according to the present invention contains one or more chemically modified nucleotides as described herein.

The nucleotides with covalent modifications of the exocyclic amino groups have been described in U.S. Pat. No. 6,001, 611, which is incorporated herein by reference. The synthesis of such nucleotides, and oligonucleotides incorporating such nucleotides are also described in the '611 patent.

According to the present invention, a suitable modification of the exocyclic amino group may be selected based on the presence of the following properties: (1) the modification interferes with but does not prevent Watson-Crick base pairing of the modified base with the complementary base in the double-stranded nucleic acid; (2) the modification interferes with but does not prevent the extension of the primer containing the modified base by the nucleic acid polymerase; (3) the modification allows synthesis of the strand complementary to the strand incorporating the modified base; and (4) the modification increases selectivity of a primer incorporating the modification.

The examples of exocyclic amino groups include the amino groups in the 6-position of adenosine, 2-position of guanosine and 4-position of cytidine. Exocyclic amino groups that take part in base pairing with the complementary nucleic acid strand may also occur in various unconventional nitrogenous bases in nucleotides. Examples of nucleosides with unconventional bases include, without limitation, 3-methyladenosine, 7-methylguanosine, 3-methylguanosine, 5-methylcytidine, and 5-hydroxymethylcytidine. Suitable modifications of exocyclic amino groups of such unconventional bases may also be selected according to the empirical method of the present invention.

The structures of the modified nucleotides containing a modified adenine, guanine, and cytosine base, respectively, are shown below,

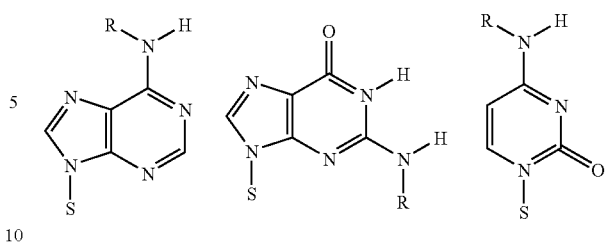

where S represents the sugar moiety, and R represents the modifier group. A variety of modifier groups are envisioned which possess the four properties outlined above. In certain embodiments, modifier groups have the structure:

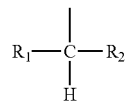

wherein $R_1$ and $R_2$ are independently selected from the group consisting of hydrogen, alkyl, alkoxy, unsubstituted or substituted aryl and phenoxy.

Alkyl groups may be branched or unbranched

Alkyl groups can be $C_1$-$C_{20}$ alkyls, for example $C_1$-$C_{10}$ alkyls.

Alkoxy groups can be $C_1$-$C_{20}$ alkoxy, for example $C_1$-$C_{10}$ alkoxy.

Aryl can be unsubstituted or substituted phenyl or naphtyl.

In one embodiment, R is a benzyl group or a substituted benzyl group. In certain embodiments, substituted benzyl groups can have the following structure:

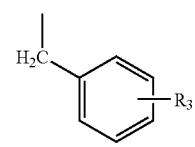

wherein $R_3$ represents a $C_1$-$C_6$ branched or unbranched alkyl group, more preferably a $C_1$-$C_4$ branched or unbranched alkyl group, an alkoxy group, or a nitro group. Preferably, $R_3$ is attached in the para-position.

In some embodiments, the modifier groups are represented by structures shown below:

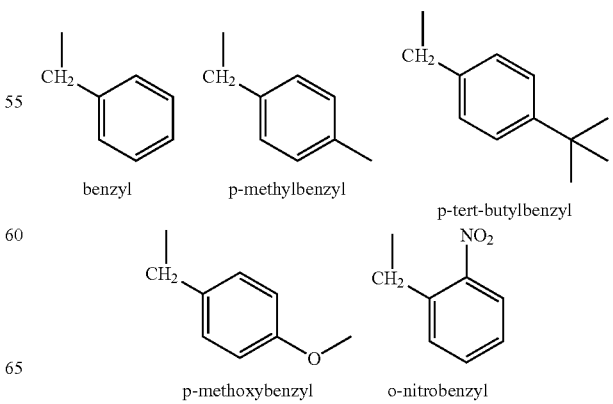

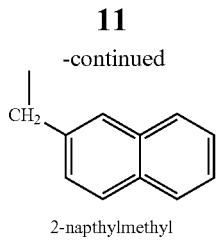

2-napthylmethyl

In general, empirical selection of a particular suitable modifier group from the class of compounds described herein can be carried out routinely by one of skill in the art, based on the presence of the four properties listed above. Preferably, suitability of a particular group is determined empirically by using the primers with modified nucleotides in an allele-specific amplification reaction. The suitability of the modification is indicated by the increased selectivity of the reaction utilizing a primer with the base modification, when compared to an identical reaction with an unmodified primer.

In some embodiments of the invention, the amplification involves the polymerase chain reaction, i.e. repeated cycles of template denaturation, annealing (hybridization) of the oligonucleotide primer to the template, and extension of the primer by the nucleotide-incorporating biocatalyst. In some embodiments, the annealing and extension occur at the same temperature step.

In some embodiments, the amplification reaction involves a hot start protocol. In the context of allele-specific amplification, the selectivity of the allele-specific primers with respect to the mismatched target may be enhanced by the use of a hot start protocol. Many hot start protocols are known in the art, for example, the use of wax, separating the critical reagents from the rest of the reaction mixture (U.S. Pat. No. 5,411,876), the use of a nucleic acid polymerase, reversibly inactivated by an antibody (U.S. Pat. No. 5,338,671), a nucleic acid polymerase reversibly inactivated by an oligonucleotide that is designed to specifically bind its active site (U.S. Pat. No. 5,840,867) or the use of a nucleic acid polymerase with reversible chemical modifications, as described e.g. in U.S. Pat. Nos. 5,677,152 and 5,773,528.

In some embodiments of the invention, the allele-specific amplification assay is the real-time PCR assay. In a real-time PCR assay, the measure of amplification is the "cycles to threshold" or Ct value. An earlier Ct value reflect the rapid achievement of the threshold level and thus a more efficient amplification. The later Ct value may reflect inefficient or inhibited amplification. In the context of an allele-specific real-time PCR assay, the difference in Ct values between the matched and the mismatched templates is a measure of the discrimination between the alleles or the selectivity of the assay.

The allele-specific amplification assay may employ any suitable nucleotide-incorporating biocatalyst known in the art. For an allele-specific PCR assay, any thermostable nucleotide incorporating biocatalyst may be used. It is sometimes desirable to use an enzyme without the proof-reading (3'-5'-exonuclease) activity, such as for example, Taq DNA polymerase. It may also be desirable to use enzymes, substantially or entirely lacking the 5'-3' nuclease activity, such as described in U.S. Pat. No. 5,795,762. One example of such an enzyme is ΔZ05 polymerase. It may sometimes be desirable to have an enzyme with a "hot start" capability, such as the reversibly modified enzymes described in U.S. Pat. Nos. 5,677,152 and 5,773,528. One example of a hot-start enzyme is ΔZ05-Gold polymerase.

Detection of the amplification products may be accomplished by any method known in the art. These methods include the use of labeled primers and probes as well as various nucleic acid-binding dyes. The means of detection may be specific to one variant of the target sequence, or may be generic to all variants of the target sequence or even to all double stranded DNA. The non-specific detection methods may be used where the amplification of the undesired variants of the target is minimal and expected to fall below the detection limit of the method.

The amplification products may be detected after the amplification has been completed, for example, by gel electrophoresis of the unlabeled products and staining of the gel with a nucleic acid-binding dye. Alternatively, the amplification products may carry a radioactive or a chemical label, either by virtue of incorporation during synthesis or by virtue of being the extension products of a labeled primer. After, or during electrophoresis, the labeled amplification products may be detected with suitable radiological or chemical tools known in the art. After electrophoresis, the product may also be detected with a target-specific probe labeled by any one of the methods known in the art. The labeled probe may also be applied to the target without electrophoresis, i.e. in a "dot blot" assay or the like.

In other embodiments, the presence of the amplification product may be detected in a homogeneous assay, i.e. an assay where the nascent product is detected during the cycles of amplification, or at least in the same unopened tube, and no post-amplification handling is required. A homogeneous amplification assay has been described for example, in U.S. Pat. No. 5,210,015. Homogeneous amplification assay using nucleic acid-intercalating dyes has been described for example, in U.S. Pat. Nos. 5,871,908 and 6,569,627. The homogeneous assay may also employ fluorescent probes labeled with two interacting fluorophores, such as "molecular beacon" probes (Tyagi et al., (1996) Nat. Biotechnol., 14:303-308) or fluorescently labeled nuclease probes (Livak et al., (1995) PCR Meth. Appl., 4:357-362). In certain variations of these technologies, an amplification product may also be identified by virtue of its distinctive melting temperature, see U.S. Pat. Nos. 5,871,908 and 6,569,627. The amplification products may also be detected using a unimolecular primer-probe combination termed "scorpion." Whitcombe et al., (1999) Detection of PCR products using self-probing amplicons and fluorescence, Nature Biotech. 17:804-807. The primer portion of the scorpion oligonucleotide may be an allele-specific primer designed according to the present invention.

In another aspect, the invention provides a reaction mixture for specifically or selectively amplifying a selected variant of the target sequence, comprising a first oligonucleotide, at least partially complementary to more than one variant of the target sequence, a second oligonucleotide, at least partially complementary to more than one variant of the target sequence, but having a 3'-terminal nucleotide complementary to only one variant of the target sequence, wherein said second oligonucleotide includes one or more nucleotides with a base, covalently modified at the exocyclic amino group, and a target nucleic acid, known to exist in more than one sequence variant. In some embodiments, the reaction mixture further comprises the reagents and solutions generally necessary for the amplification of nucleic acids, including a nucleotide-incorporating biocatalyst, nucleic acid precursors, i.e. nucleoside triphosphates, and organic and inorganic ions, suitable for the support of the activity of the nucleotide-incorporating biocatalyst.

In another aspect, the invention provides kits for conducting allele-specific amplification according to the invention. The kit generally includes assay-specific components as well as components generally required for performing DNA amplification assays. As the assay-specific components, the allele-specific amplification kit of the present invention typically includes at least one allele-specific oligonucleotide, at least partially complementary to more than one variant of the target sequence, having a 3'-terminal nucleotide complementary to only one variant of the target sequence and also having one or more nucleotides with a base covalently modified at the exocyclic amino group, optionally, a second oligonucleotide, at least partially complementary to more than one variant of the target sequence and optionally a control nucleic acid sequence comprising an amount of at least one variant of the control target sequence, at least partially complementary to the oligonucleotides enclosed in the kit. In some embodiments, more than one variant of the control nucleic acid sequence may be enclosed. In certain embodiments, among the several variants of the control nucleic acid sequence enclosed in the kit, at least one variant is complementary to the 3'-terminal nucleotide of the allele-selective oligonucleotide. As the components generally required for nucleic acid amplification, the kit of the present invention typically includes one or more of a nucleotide incorporating biocatalyst, nucleic acid precursors, such as nucleoside triphosphates (deoxyribonucleoside triphosphates or ribonucleoside triphosphates), optionally, a pyrophosphatase, for minimizing pyrophosphorolysis of nucleic acids, a uracil N-glycosylase (UNG) for protection against carry-over contamination of amplification reactions, pre-made reagents and buffers necessary for the amplification reaction and detection, and a set of instructions for conducting allele-specific amplification of the present invention.

In yet another aspect, the invention provides an oligonucleotide for use in allele-specific PCR. A typical oligonucleotide for use in allele-specific PCR of the present invention comprises 10-50, more preferably 15-35 nucleotides, the majority of them complementary to a sequence in more then one variant of the target sequence. However, the 3'-terminal nucleotide of the oligonucleotide is complementary to one variant of the target sequence and not complementary to other variants. Further, the oligonucleotide of the present invention includes one or more nucleotides with a base covalently modified at the exocyclic amino group. In some embodiments, the modified-base nucleotide occurs between 1 and 30, for example between 1 and 10, between 1 and 5, or for example 1, 2 or 3 nucleotides upstream of the 3'-terminal nucleotide. In other embodiments, the modified-base nucleotide is the 3'-terminal nucleotide. In some embodiments, the modified-base nucleotide occurs both at the 3'-terminus as well as elsewhere within the oligonucleotide.

Without being bound by a particular theory, the inventors hypothesize that the covalent base modifications of the present invention, especially the bulky groups, destabilize, but do not entirely disrupt hydrogen bonding in the context of Watson-Crick base pairing between the primer and the template nucleic acid. When the modification is combined with a non-complementary base at the same or nearby position within the primer (as on the undesirable or "mismatched" variant of the target sequence), the combined weakness of hydrogen bonding destabilizes the primer-target nucleic acid complex to the extent that the extension of the oligonucleotide by the nucleotide-incorporating biocatalyst is partially or completely inhibited. However, when the modification of the base is present alone, without the non-complementary base (as on the desirable or "matched" variant of the target sequence, which is to be amplified), the primer is extended efficiently. FIG. 1 is a diagram illustrating the position of the polymorphism and the primer modifications, and their role in allowing the amplification or the matched target but inhibiting the amplification of the mismatched target.

The following examples and figures are provided to aid the understanding of the present invention, the true scope of which is set forth in the appended claims. It is understood that modifications can be made in the procedures set forth without departing from the spirit of the invention.

EXAMPLES

The examples below utilize a "matched" and a "mismatched" target. As used in the examples, the matched target is designed to be complementary to the allele-specific amplification primer. The mismatched target is designed to have a mismatch with the 3'-terminal nucleotide of the allele-specific primer.

As a matched target, the examples utilize the V600E mutation of the human BRAF gene. This mutation is a valine-to-glutamate change of amino acid 600, that results from a thymine (T) to adenine (A) transition at nucleotide 1799 of the BRAF gene. The mutation is found in many cancers and is thought to contribute to cancer progression, as it results in constitutive activation of the MAPK pathway. Detection of this single nucleotide change in a population of tumor cells has utility in the diagnosis and treatment of human cancers.

The mutant target is "matched", i.e. forms an A-T Watson-Crick pair with the 3'-terminal nucleotide of each of the allele-specific primers (Table 1). The mismatched target is the wild-type BRAF sequence. The mismatched target forms an A-A mismatch with the 3'-terminal nucleotide of the allele-specific primers.

TABLE 1

Primers and probes

Allele-specific primers

| | |
|---|---|
| SEQ ID NO: 3 | 5'-AGTAAAAATAGGTGATTTTGGTCTAGCTACAGA-3' |
| SEQ ID NO: 4 | 5'-AGTAAAAATAGGTGATTTTGGTCTAGCTAC<u>X</u>GA-3' |
| SEQ ID NO: 5 | 5'-AGTAAAAATAGGTGATTTTGGTCTAGCTAC<u>Y</u>GA-3' |
| SEQ ID NO: 7 | 5'-AGTAAAAATAGGTGATTTTGGTCTAGCTACAG<u>Y</u>-3' |
| SEQ ID NO: 8 | 5'-AGTAAAAATAGGTGATTTTGGTCTAGCT<u>Y</u>CAG<u>Y</u>-3' |
| SEQ ID NO: 10 | 5'-AGTAAAAATAGGTGATTTTGGTCTAGCTACAG<u>X</u>-3' |
| SEQ ID NO: 11 | 5'-TAAAAATAGGTGATTTTGGTCTAGCT<u>X</u>CAG<u>X</u>-3' |

Other primers and probes

| | |
|---|---|
| SEQ ID NO: 6 | 5'-TAGCCTCAATTCTTACCATCCACA<u>X</u>-3' |
| SEQ ID NOS 9 and 16 | 5'-FTCGATGGAGTQGGGTCCCATCAGTTTGAACA-GTTGTCTp-3' |

X - N[6]-benzyl-dA
Y - N[6]-para-tert-butyl-benzyl-dA
F - cx-FAM donor fluorophore
Q - BHQ-2 "Black Hole" quencher
p - 3'-phosphate
The 3'-terminal nucleotide corresponds to the variable position in the target

Example 1

Allele-Specific Amplification Using Primers with Internal Base Modifications In this example, two variants of the template sequence were present in equal amounts, a matched variant, complementary to the primer sequence and a mismatched variant. The matched variant was a plasmid DNA with the insert incorporating the BRAF V600E mutant sequence (SEQ ID NO: 1), while the mismatched variant was the same plasmid with the BRAF wild-type sequence (SEQ ID NO: 2).

```
(BRAF V600E mutant sequence fragment):
                                    SED ID NO: 1
5'-AGTAAAAATAGGTGATTTTGGTCTAGCTACAGAGAAATCTCGATGGA

GTGGGTCCCATCAGTTTGAACAGTTGTCTGGATCCATTTTGTGGATGGTA

AGAATTGAGGCTA-3'

(BRAF wild-type sequence fragment):
                                    SEQ ID NO: 2
5'-AGTAAAAATAGGTGATTTTGGTCTAGCTACAGTGAAATCTCGATGGA

GTGGGTCCCATCAGTTTGAACAGTTGTCTGGATCCATTTTGTGGATGGTA

AGAATTGAGGCTA-3'
```

The forward primers (SEQ ID NO: 3, 4, 5) and the reverse primer (SEQ ID NO: 6) are shown in Table 1. The primers contained an internal $N^6$-benzyl-dA or an internal $N^6$-para-tert-butyl-benzyl-dA where indicated.

Each 100 µL reaction contained $10^6$ copies of either target, 5% glycerol, 50 mM tricine (pH 8.3), 25 mM potassium acetate (pH 7.5), 200 µM each dATP, dCTP and dGTP, 400 µM dUTP, 0.1 µM or one of the forward primers (SEQ ID NO: 3, 4 or 5), 0.7 µM reverse primer (SEQ ID NO: 6), 2 µM Syto-13 intercalating dye, 1% DMSO, 4 units uracil-N-glycosylase (UNG), 10 units ΔZ05 polymerase, and 4 mM magnesium acetate.

Amplification and analysis were done using the Roche LightCycler 480 instrument. The reactions were subjected to the following temperature profile: 50° C. for 5 minutes (UNG step), 95° C. for 10 minutes, followed by 80 cycles of 95° C. for 15 seconds and 59° C. for 40 seconds. Fluorescence data was collected at the end of each 59° C. step.

Figure 2:
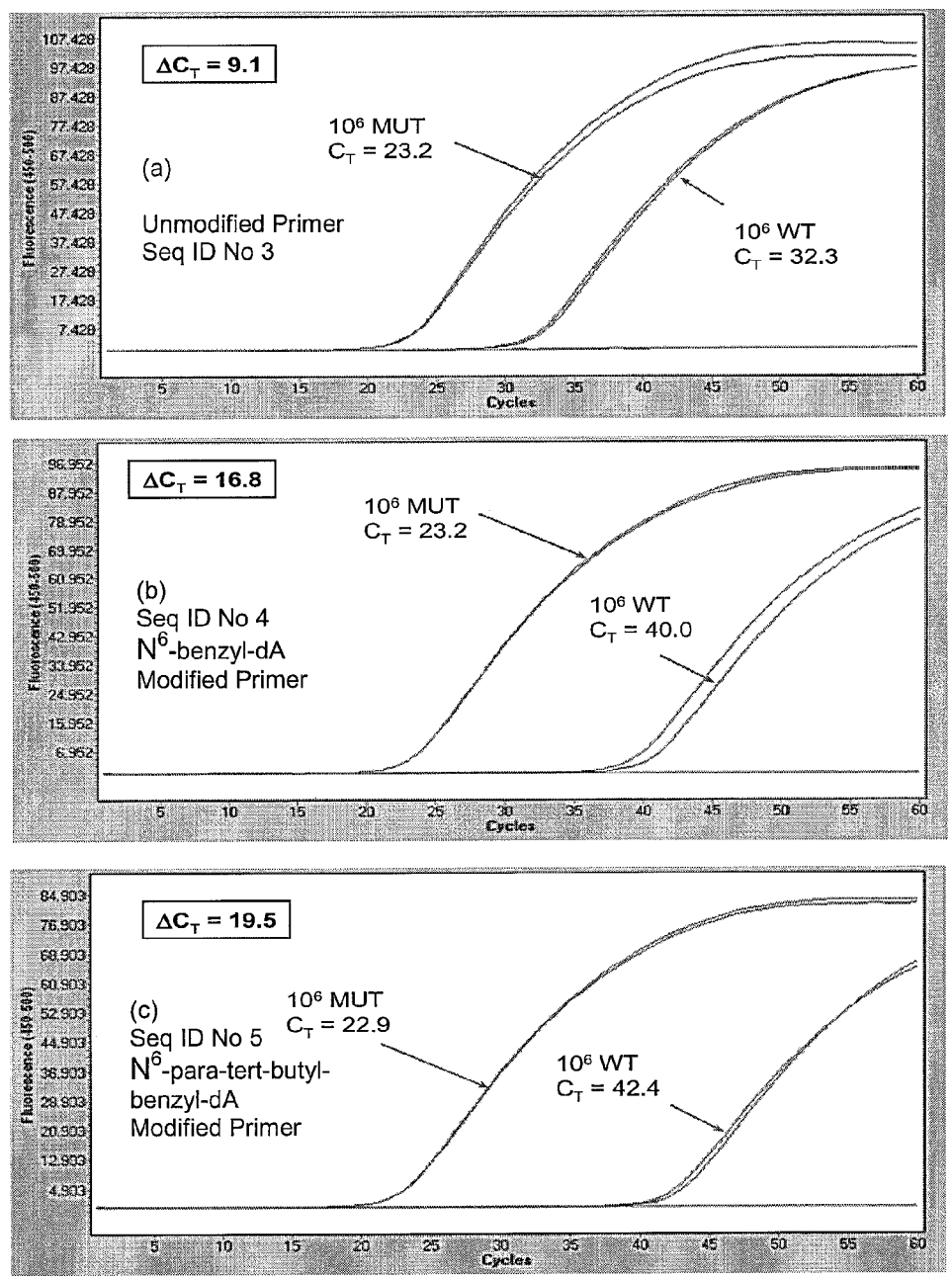
FIG. 2 shows the results of allele-specific amplification using primers with internal base modifications.

The results are shown on FIG. 2. The amplification results are expressed as a change in fluorescence in the 450-500 nm wavelength interval. The selectivity of the amplification is measured by the difference in the Ct value (ΔCt) between the matched and the mismatched targets. ΔCt for each experiment is indicated on FIG. 2. The data shows that the matched (mutant) variant of the target was amplified selectively over the mismatched (wild-type) variant. The selectivity was enhanced by the base modification of the nucleotides in the primers.

Example 2

Allele-Specific Amplification Using Primers with One or More Internal and 3'-Terminal Base Modifications For this experiment, the same matched (mutant) and mismatched (wild-type) targets as in Example 1 were used. The primers contained base modifications at an internal position, 3'-terminal position or both.

Each 100 µL reaction contained $10^6$ copies of either target, 5% glycerol, 50 mM tricine (pH 8.3), 90 mM potassium acetate (pH 7.5), 200 µM each dATP, dCTP and dGTP, 400 µM dUTP, 0.5 µM of one of the forward primers (SEQ ID NO: 3, 5, 7 or 8), 0.5 µM reverse primer (SEQ ID NO: 6), 0.2 µM fluorogenic probe (SEQ ID NOS 9 and 16), 1% DMSO, 4 units uracil-N-glycosylase (UNG), 10 units Z05 polymerase, and 5 mM magnesium acetate.

Amplification and analysis were done using the Roche LightCycler 480 instrument. Reactions were subjected to the following temperature profile: 50° C. for 5 minutes (UNG step), 95° C. for 10 minutes, followed by 60 cycles of 95° C. for 15 seconds and 59° C. for 40 seconds. Fluorescence data was collected at the end of each 59° C. step.

Figure 3:
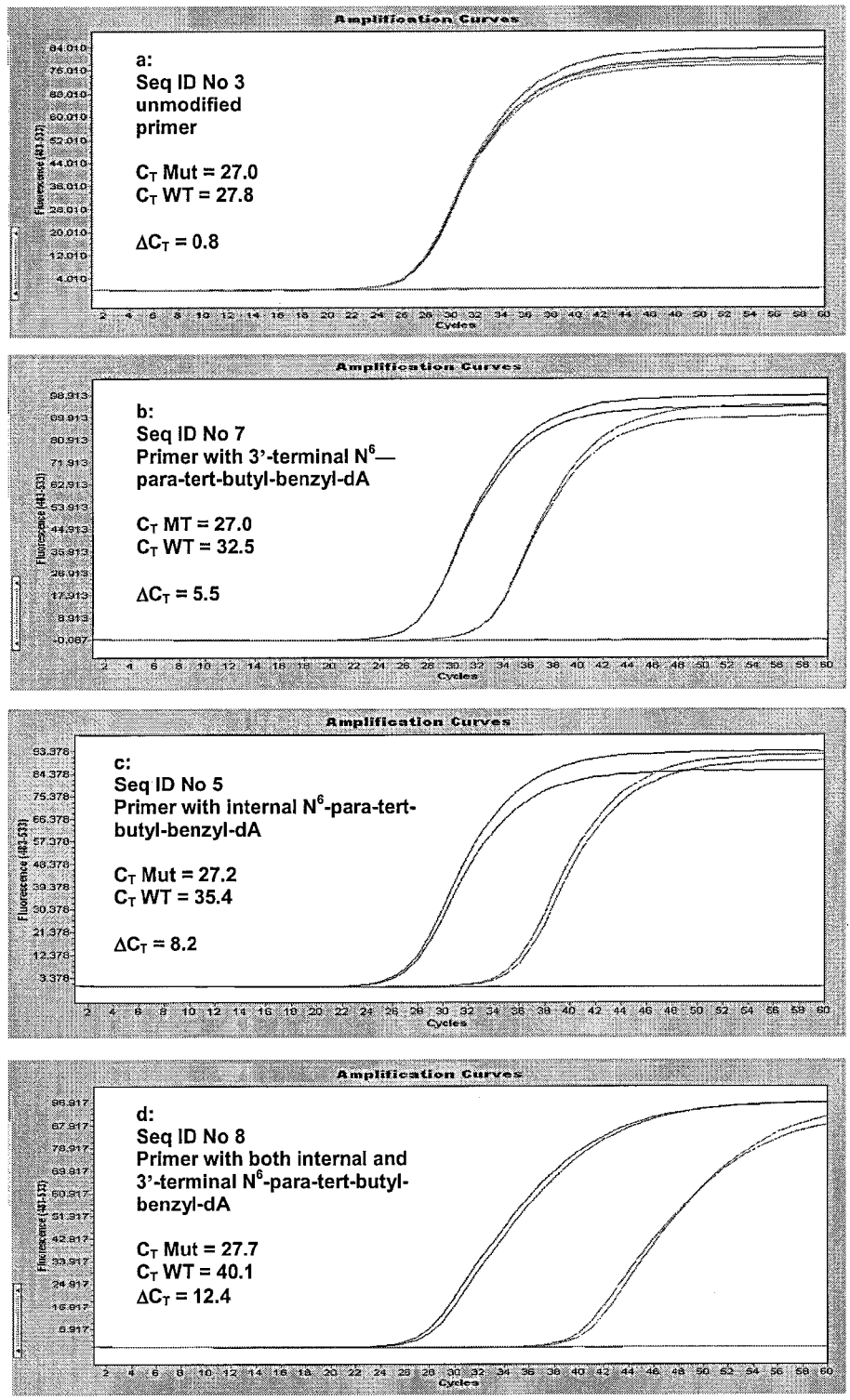
FIG. 3 shows the results of allele-specific amplification using primers with one or more internal and 3'-terminal base modifications.

The results are shown on FIG. 3 in the same format as the results of the Example 1, except the fluorescence is measured in the 483-553 nm wavelength interval. The data demonstrates that the base modifications of the primer improve the selectivity of the amplification assay, and several modified bases may have a cumulative effect on selectivity.

Example 3

Allele-Specific Amplification Using a Primer with a Base Modification and Various DNA Polymerases In this example, the same matched (mutant) and mismatched (wild-type) targets as in Example 1, where amplified using a primer with a single internal base modification. The amplification was carried out in the presence of Z05, ΔZ05, or ΔZ05-Gold polymerase.

The Z05 reactions contained $10^6$ copies of template, 5% glycerol, 50 mM tricine (pH 8.3), 90 mM potassium acetate (pH 7.5), 200 µM each dATP, dCTP, and dGTP, 400 µM dUTP, 0.5 µM forward primer (SEQ ID NO: 5), 0.5 µM reverse primer (SEQ ID NO: 6), 2 µM Syto-13 intercalating dye, 1% DMSO, 4 units uracil-N-glycosylase (UNG), 10 units of Z05 polymerase, and 5 mM magnesium acetate in 100 µL.

The ΔZ05 reactions contained $10^6$ copies of template, 5% glycerol, 50 mM tricine (pH 8.3), 25 mM potassium acetate (pH 7.5), 200 µM each dATP, dCTP and dGTP, 400 µM dUTP, 0.1 µM forward primer (SEQ ID NO: 5), 0.7 µM reverse primer (SEQ ID NO: 6), 2 µM Syto-13 intercalating dye, 1% DMSO, 4 units uracil-N-glycosylase (UNG), 10 units ΔZ05 polymerase, and 4 mM magnesium acetate in 100 µL.

The ΔZ05-Gold reactions contained $10^6$ copies of template, 8% glycerol, 50 mM tricine (pH7.7), 45 mM potassium acetate (pH 7.5), 200 µM each dATP, dCTP and dGTP, 400 µM dUTP, 0.1 µM forward primer (SEQ ID NO: 5), 0.7 µM reverse primer (SEQ ID NO: 6), 2 µM Syto-13 intercalating dye, 1% DMSO, 2 units uracil-N-glycosylase (UNG), 60 units ΔZ05-Gold polymerase, and 3 mM magnesium acetate in 100 µL.

Figure 4:
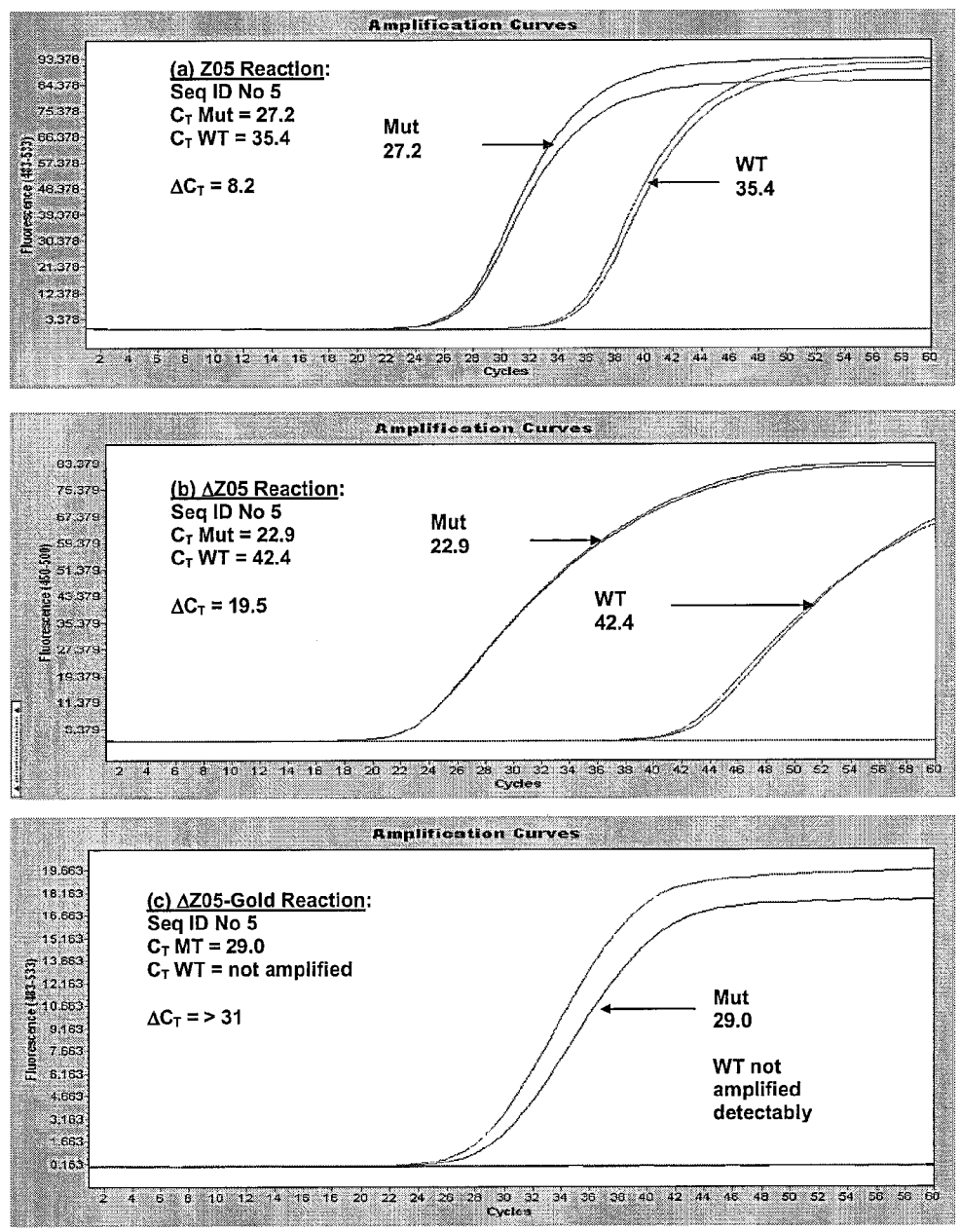
FIG. 4 shows the results of allele-specific amplification using a primer with a base modification and various DNA polymerases.

The results are shown on FIG. 4 in the same format as the results of the Example 2. The data demonstrates the relative ability of each enzyme to perform allele-selective amplification using base-modified primers.

Example 4

Allele-Specific Amplification Using Base-Modified Primers in the Presence of Excess Amounts of Mismatched Template In this example, the same matched (mutant) and mismatched (wild-type) targets as in Example 1 were used. The targets were amplified using a primer with a single internal alkyl modification. To simulate clinical samples, the reactions contained an extremely low copy number of the mutant (matched) target alone or in the presence of large excess of the wild-type (mismatched) target. In a separate reaction, a large amount of the mismatched target was present without any matched target.

The 100 μL it reactions contained the indicated amount of target DNA, 8% glycerol, 50 mM tricine (pH7.7), 45 mM potassium acetate (pH 7.5), 200 μM each dATP, dCTP and dGTP, 400 μM dUTP, 0.1 μM forward primer (SEQ ID NO: 5), 0.7 μM reverse primer (SEQ ID NO: 6), 0.2 μM fluorogenic probe (SEQ ID NOS 9 and 16), 1% DMSO, 2 units uracil-N-glycosylase (UNG), 60 units ΔZ05-Gold polymerase, and 3 mM magnesium acetate.

Figure 5:
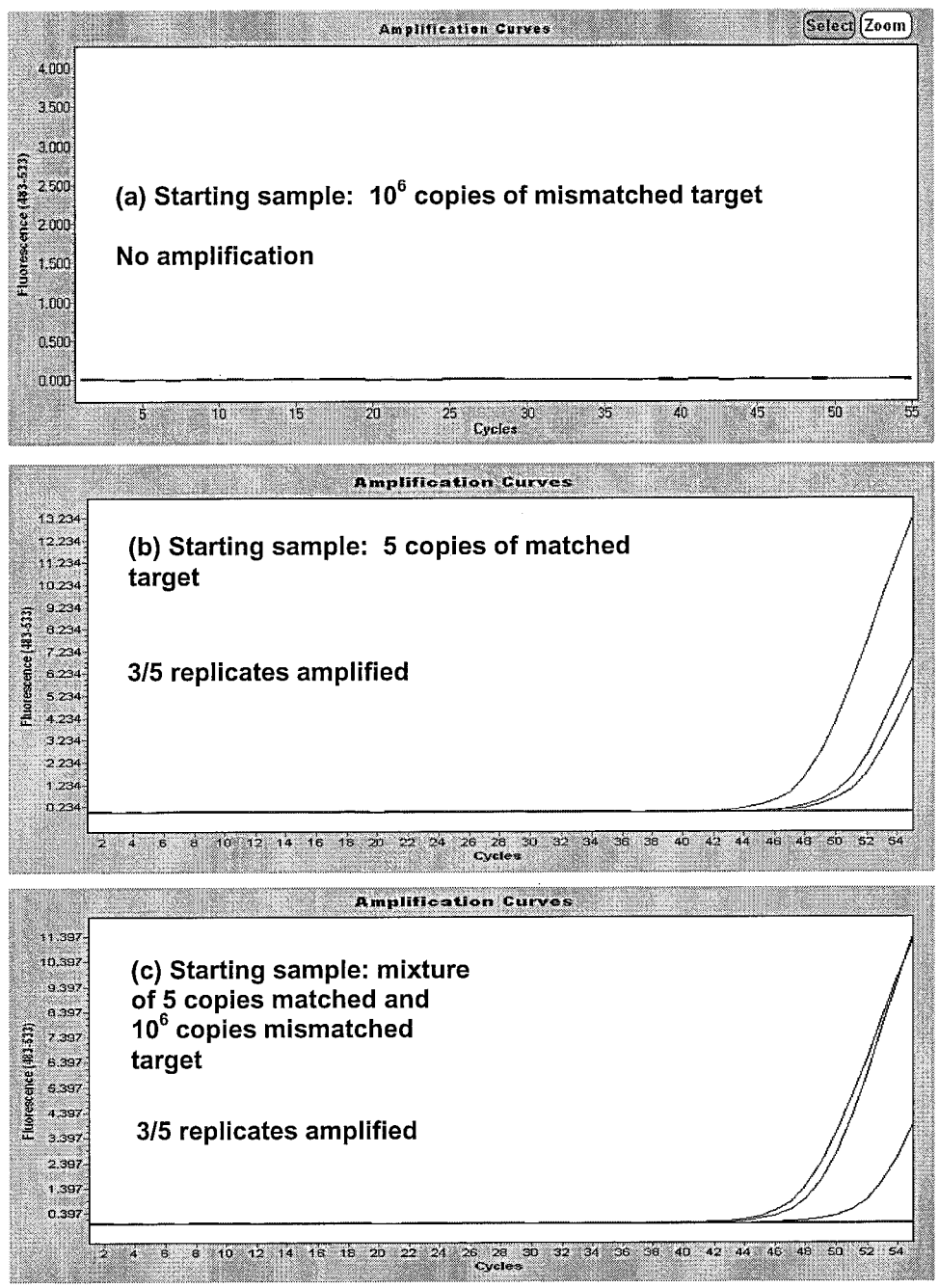
FIG. 5 shows the results of allele-specific amplification using base-modified primers in the presence of excess amounts of mismatched template.

The results are shown in FIG. 5 in the same format as the results of the Example 2. The data demonstrates that under the exemplary conditions, amplification is specific to the matched target, regardless of the presence or relative amount of the mismatched target.

Example 5

Allele-Specific Amplification Using Scorpion Arms-Like Primers with Internal Base Modifications

TABLE 3

| SEQ ID NO | FUNCTION | PRIMER SEQUENCE |
|---|---|---|
| 3 | FORWARD PRIMER | 5'-AGTAAAAATAGGTGATTTTGGTCTAGCTACAG<u>A</u>-3' |
| 12 and 17 | FORWARD PRIMER, PROBE | 5'-FCCCGCGCGGACCCACTCCATCGAGAGCGCG GGQJAGTAAAAATAGGTGATTTTGGTCTAGCTACAG<u>A</u>-3' |
| 5 | FORWARD PRIMER | 5'-AGTAAAAATAGGTGATTTTGGTCTAGCTACYG<u>A</u>-3' |
| 13 and 18 | FORWARD PRIMER, PROBE | 5'-FCCCGCGCGGACCCACTCCATCGAGAGCGCG GGQJAGTAAAAATAGGTGATTTTGGTCTAGCTACYG<u>A</u>-3' |

TABLE 3-continued

| SEQ ID NO | FUNCTION | PRIMER SEQUENCE |
|---|---|---|
| 14 | REVERSE PRIMER | 5'-TAGCCTCAATTCTTACCATCCACAX-3' |
| 15 | PROBE | 5'-FTCTCGATGGAGTGGGTCCQp-3' |

X - N$^6$-benzyl-dA
Y - N$^6$-para-tert-butyl-benzyl-dA
F - cx-FAM donor fluorophore
Q - BHQ-2 "Black Hole" quencher
J - HEG
p - 3'-phosphate
*The allele selective nucleotide is underlined (N or N-1 position from 3' terminus)

In this example, two variants of the template sequence were present in equal amounts, a matched variant, complementary to the primer sequence and a mismatched variant. The matched variant was a plasmid DNA with the insert representing the BRAF V600E mutant sequence (SEQ ID NO: 1), while the mismatched variant was the same plasmid with the BRAF wild-type sequence (SEQ ID NO: 2). The forward primers (SEQ ID NO: 3, 5, 12, 13, 17 and 18) and reverse primer (SEQ ID NO: 14) are as described in Table 3. The forward, ASPCR primers, were designed with the SNP at the 3' terminal position, either with or without N6-tert-butyl-benzyl-dA modification. The ASPCR primer is paired with a downstream detection probe (SEQ ID NO: 15) or linked to the probe complement in a closed Scorpion-like format.

Each 50 uL reaction contained $10^5$ copies of either target, 5% glycerol, 50 mM tricine (pH 8.3), 150 mM potassium acetate (pH 7.5), 200 μM each of dATP, dCTP and dGTP, 400 μM dUTP, 0.4 μM forward primer, 0.4 μM reverse primer, 1% DMSO, 2 units uracil-N-glycosylase (UNG), 10 units Z05 polymerase, and 3 mM magnesium acetate. 0.2 uM of detection probe was added to reactions containing Primers 3 and 5 where the probe complement is not linked to the forward primer.

Amplification and analysis were done using the Roche LightCycler 480 instrument. The reactions were subjected to the following temperature profile: 50° C. for 5 minutes (UNG step) followed by 95 cycles of 95° C. for 15 seconds and 59° C. for 40 seconds. Fluorescence data was collected at the 495-525 nm range at the end of each 59° C. anneal/extend step.

Figure 6:
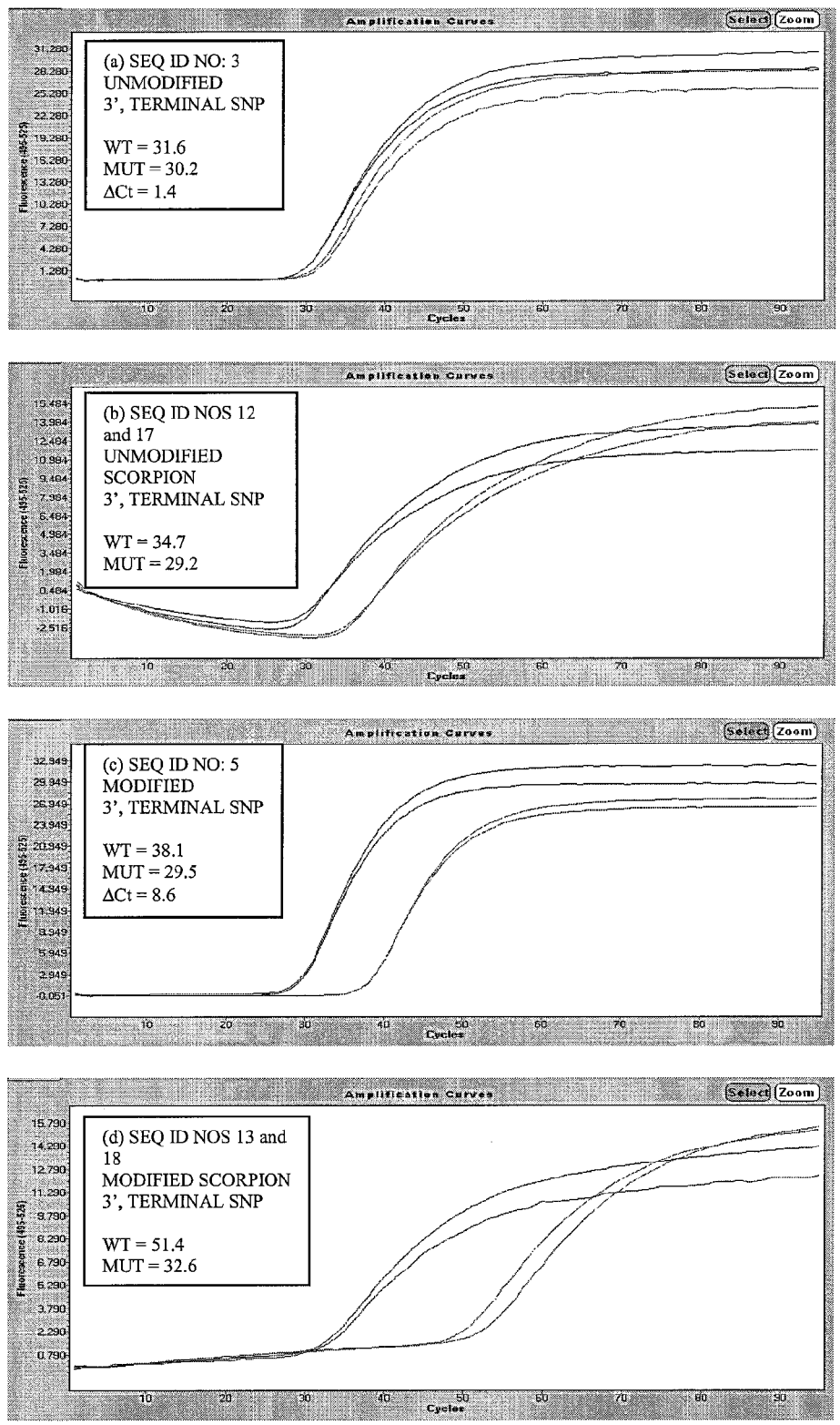
FIG. 6 shows an example of a scorpion or scorpion-like probe-primer format within the meaning of the invention.

The results are shown on FIG. 6 and Table 4. The selectivity of the amplification is measured by the difference in the Ct value (ΔCt) between the matched and the mismatched targets. ΔCt for each experiment is indicated on each diagram and summarized in Table 4. The data shows that the matched (mutant) variant of the target was amplified selectively over the mismatched (wild-type) variant using either the individual primer and probe or the primer and probe linked in a closed Scorpion-like format.

TABLE 4

| SEQ ID NO | PRIMER SEQUENCE | POSITION OF SELECTIVE NUCLEOTIDE | PRIMER FORMAT | MODIFICATION OF PRIMING SEGMENT | WT $CT_{AVG}$ | MUT $CT_{AVG}$ | ΔCT |
|---|---|---|---|---|---|---|---|
| 3 | AGTAAAAATAGGTGATTTTGGTCTA GCTACAG<u>A</u> | 3' terminus | Traditional | none | 31.6 | 30.2 | 1.4 |
| 12 and 17 | FCCCGCGCGGACCCACTCCATCGAG AGCGCGGGQJAGTAAAAATAGGTGA TTTTGGTCTAGCTACAG<u>A</u> | 3' terminus | Scorpion ARMS | none | 34.7 | 29.2 | 5.5 |
| 5 | AGTAAAAATAGGTGATTTTGGTCTA GCTACYG<u>A</u> | 3' terminus | Traditional | Y at N-2 | 38.1 | 29.5 | 8.6 |

TABLE 4-continued

| SEQ ID NO | PRIMER SEQUENCE | POSITION OF SELECTIVE NUCLEOTIDE | PRIMER FORMAT | MODIFICATION OF PRIMING SEGMENT | WT CT$_{AVG}$ | MUT CT$_{AVG}$ | ΔCT |
|---|---|---|---|---|---|---|---|
| 13 and 18 | FCCCGCGCGGACCCACTCCATCGAG AGCGCGGGQJAGTAAAAATAGGTGA TTTTGGTCTAGCTACYGA | 3' terminus | Scorpion ARMS | Y at N-2 | 51.4 | 32.6 | 18.8 |

While the invention has been described in detail with reference to specific examples, it will be apparent to one skilled in the art that various modifications can be made within the scope of this invention. Thus the scope of the invention should not be limited by any of the examples described herein, but by the claims presented below. All publications including patent applications and patents cited in this application are incorporated by reference in their entirety for all purposes to the same extent as if each individual publications were individually indicated to be incorporated by reference for all purposes.

The invention claimed is:

1. A method of allele-specific amplification of a variant of a target sequence, which exists in the form of several variant sequences, comprising (a) providing a sample, possibly containing at least one variant of a target sequence;

(b) providing a first oligonucleotide, at least partially complementary to one or more variants of the target sequence;

(c) providing a second oligonucleotide, at least partially complementary to one or more variants of the target sequence, having a 3'-terminal nucleotide complementary to only one variant of the target sequence; wherein said second oligonucleotide incorporates at least one nucleotide with a base covalently modified at the exocyclic amino group;

(d) providing conditions suitable for the hybridization of said first and second oligonucleotides to at least one variant of the target sequence; and (e) providing conditions suitable for the oligonucleotide extension by a nucleotide-incorporating biocatalyst; wherein said biocatalyst is capable of extending said second oligonucleotide when it is hybridized to the variant of the target sequence for which it has said complementary 3'-terminal nucleotide, and substantially less when said second oligonucleotide is hybridized to the variant of the target sequence for which it has a non-complementary 3'-terminal nucleotide.

2. The method of claim 1, wherein the nucleotide having a covalently modified base at the exocyclic amino group is located at positions −5, −4, −3, −2 or −1 relative to the 3'-terminus of the second oligonucleotide.

3. The method of claim 1, wherein said nucleotide-incorporating biocatalyst in step (e) is capable of extending said second oligonucleotide, exclusively when said oligonucleotide is hybridized to the variant of the target sequence to which it has said complementary 3'-terminal nucleotide.

4. The method of claim 1, wherein said base, covalently modified at the exocyclic amino group is selected from a group consisting of $N^6$-benzyl-adenine, $N^6$-para-tert-butyl-benzyl adenine, $N^2$-alkyl-guanine and $N^4$-benzyl-cytosine.

5. The method of claim 1, further comprising a step (f) of detecting the product of said amplification.

6. The method of claim 1 wherein said nucleotide incorporating biocatalyst is substantially lacking the 5'-3' nuclease activity.

7. The method of claim 1, wherein said nucleotide-incorporating biocatalyst is selected from a group consisting of Taq DNA polymerase, Z05 DNA polymerase, ΔZ05 DNA polymerase and ΔZ05-Gold DNA polymerase.

8. The method of claim 1, wherein said target sequence, which exists in the form of several variant sequences is SEQ ID NO:2 and variants thereof.

9. The method of claim 1, wherein the second oligonucleotide has a scorpion or scorpion-like format.

10. The method of claim 7, wherein said variant of the sequence in step (a) is SEQ ID NO: 1.

11. The method of claim 7, wherein said first oligonucleotide is SEQ ID NO: 6.

12. The method of claim 7, wherein said second oligonucleotide is selected from a group consisting of SEQ ID NOs: 4, 5, 7, 8, 10, 11, 12, 13, 17 and 18.

13. A method of detecting a variant of a target sequence in a sample, which exists in the form of several variant sequences comprising
 (a) hybridizing a first and second oligonucleotides to at least one variant of the target sequence; wherein the first oligonucleotide is at least partially complementary to one or more variant of the target sequence and the second oligonucleotide is at least partially complementary to one or more variant of the target sequence and has a 3'-terminal nucleotide complementary to only one variant of the target sequence, said second oligonucleotide incorporating at least one nucleotide with a base covalently modified at the exocyclic amino group;
 (b) extending the second oligonucleotide with a nucleotide-incorporating biocatalyst; wherein said biocatalyst is capable of detectably extending only the oligonucleotide, hybridized to the variant of the target sequence for which it has said complementary 3'-terminal nucleotide; and
 (c) detecting the products of said second oligonucleotide extension, wherein the extension signifies the presence of the variant of a target sequence to which the oligonucleotide has a complementary 3'-terminal nucleotide.

\* \* \* \* \*